US010299940B2

(12) United States Patent
Kloke

(10) Patent No.: US 10,299,940 B2
(45) Date of Patent: May 28, 2019

(54) METHOD AND DEVICE FOR PRODUCING A THREE-DIMENSIONAL, MULTI-CELL OBJECT

(71) Applicant: TECHNISCHE UNIVERSITAET BERLIN, Berlin (DE)

(72) Inventor: Lutz Kloke, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 16 days.

(21) Appl. No.: 15/525,368

(22) PCT Filed: Nov. 10, 2015

(86) PCT No.: PCT/EP2015/076138
§ 371 (c)(1),
(2) Date: May 9, 2017

(87) PCT Pub. No.: WO2016/075103
PCT Pub. Date: May 19, 2016

(65) Prior Publication Data
US 2017/0319358 A1 Nov. 9, 2017

(30) Foreign Application Priority Data

Nov. 10, 2014 (EP) .................................... 14192461

(51) Int. Cl.
*B33Y 10/00* (2015.01)
*B29C 64/124* (2017.01)
*B29C 64/129* (2017.01)
*B29C 64/135* (2017.01)
(Continued)

(52) U.S. Cl.
CPC ............ *A61F 2/5046* (2013.01); *A61L 27/36* (2013.01); *B29C 64/124* (2017.08); *B33Y 70/00* (2014.12); *B33Y 80/00* (2014.12); *G03F 7/0037* (2013.01)

(58) Field of Classification Search
CPC .... B29C 64/124; B29C 64/129; B29C 64/135
See application file for complete search history.

(56) References Cited

U.S. PATENT DOCUMENTS 8,580,546 B2  11/2013 Gonda et al.
8,741,203 B2  6/2014 Liska et al.
(Continued)

FOREIGN PATENT DOCUMENTS

EP  1935620 A2  6/2008
EP  1935620 A3  7/2010
(Continued)

OTHER PUBLICATIONS

International Search Report for PCT/EP2015/076138, English translation attached to original, Both completed by the European Patent Office dated Jan. 29, 2016, 7 Pages.
(Continued)

*Primary Examiner* — Vu A Nguyen
(74) *Attorney, Agent, or Firm* — Brooks Kushman P.C.

(57) ABSTRACT

A method for producing a three-dimensional, multi-cell object, in which polymerized structures are produced in layers by the irradiation of light radiation. To this end, use is made of photopolymerizable liquids which at least partly comprise biological cells. The invention also relates to a device for carrying out such a method and to the use of this device for producing an artificial organ.

11 Claims, 3 Drawing Sheets

Figure 1:
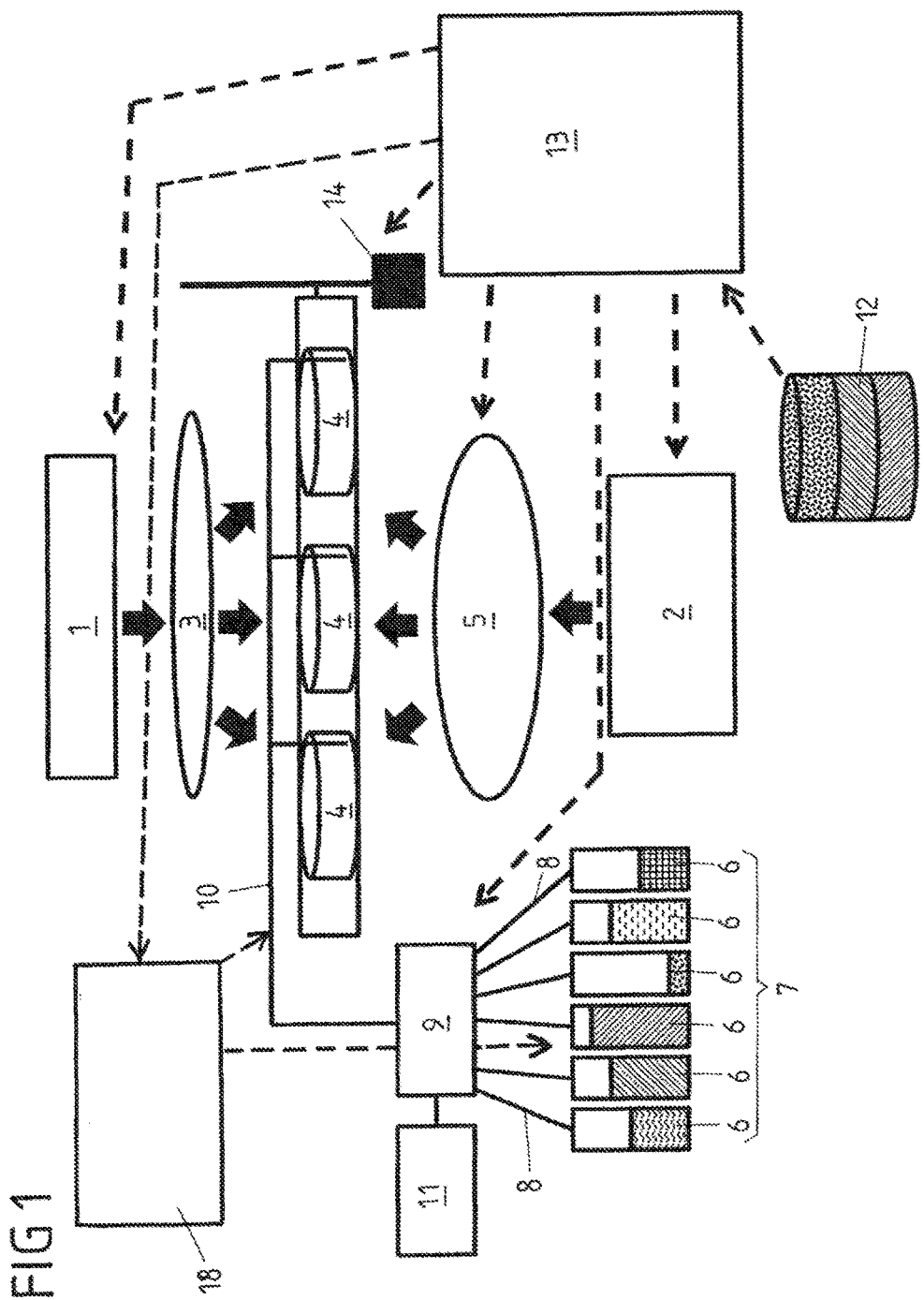

(51) Int. Cl.

| | | |
|---|---|---|
| *A61F 2/50* | (2006.01) | |
| *G03F 7/00* | (2006.01) | |
| *B33Y 80/00* | (2015.01) | |
| *B33Y 70/00* | (2015.01) | |
| *A61L 27/36* | (2006.01) | |

(56) References Cited

U.S. PATENT DOCUMENTS

| | | |
|---|---|---|
| 2009/0208466 A1 | 8/2009 | Yoo et al. |
| 2011/0076734 A1 | 3/2011 | Zhou et al. |
| 2011/0250688 A1 | 10/2011 | Hasan |
| 2011/0309554 A1 | 12/2011 | Liska et al. |
| 2011/0313542 A1 | 12/2011 | Forgacs et al. |
| 2012/0288938 A1 | 11/2012 | Forgacs et al. |
| 2014/0093932 A1 | 4/2014 | Murphy et al. |

FOREIGN PATENT DOCUMENTS

| | | | |
|---|---|---|---|
| WO | 9948541 | 9/1999 | |
| WO | 2010045951 | 4/2010 | |
| WO | 2013113883 | 8/2013 | |
| WO | 2013158508 | 10/2013 | |
| WO | 2014126830 A2 | 8/2014 | |
| WO | 2014126830 A3 | 8/2014 | |
| WO | WO-2014126830 A2 * | 8/2014 | ........... G03F 7/0037 |

OTHER PUBLICATIONS

Singapore Written opinion for Application No. SG11201703635P, dated Nov. 16, 2017, 6 Pages.

\* cited by examiner

METHOD AND DEVICE FOR PRODUCING A THREE-DIMENSIONAL, MULTI-CELL OBJECT

CROSS-REFERENCE TO RELATED APPLICATION

This application is the U.S. national phase of PCT Application No. PCT/EP2015/076138 filed on Nov. 10, 2015, which claims priority to EP Patent Application No. 14192461.3 filed on Nov. 10, 2014, the disclosures of which are incorporated in their entirety by reference herein.

The present invention relates to a method for producing a three-dimensional, multi-cell object, a device for producing a three-dimensional, multi-cell object, and use of such a device.

Three-dimensional multi-cell objects can also be referred to as cellular objects of biological material. The production of such objects by so-called bioprinting methods is known. Here, the term "printing" refers to the three-dimensional structuring of biological material. Ordinarily, biological cells are formed in a previously selected structure by means of a gel. The processes used for such bioprinting methods are so-called inkjet printing, so-called syringe printing or bioplotting, and so-called laser printing. Each of these three processes has specific advantages, but also limitations.

In the inkjet printing method, cells in a liquid are propelled onto a carrier by means of a piezo-nozzle. This process works similarly to the commercial paper-inkjet printing process, with the sole exception that a biological ink in the form of a carrier liquid with cells suspended therein is used instead of ink for printing. By means of this process, extremely fine amounts can be printed, but the precision of the method leaves something to be desired, as the drops produced by the piezo-nozzles are propelled with biological cells in the carrier liquid from the piezo-nozzles and must fly through the air over the distance between the ends of the piezo-nozzles and the surfaces intended to receive the object to be printed. The drops undergo deformations in flight, causing them to undergo a wobbling motion during the flight. This leads to inaccuracies with such an inkjet printer, as the cells do not always reach their intended location. Furthermore, a three-dimensional layered structure of the object to be produced is limited, as layering can only be carried out from above, making it difficult to produce support structures and overhanging structures.

Such inkjet printing methods are described for example in WO 99/48541 A1, US 2009/0208466 A1, US 2011/0076734 A1, and US 2011/0250688 A1.

The syringe printing method is currently the most commonly used printing method in the bioprinting field. In this method, the material to be printed is loaded into a syringe and forced out of the syringe by means of compressed air or punching pressure. The nozzle of the syringe in this case is moved into its intended position by an x-y-z movement unit in accordance with the object to be printed. A specified amount of the printing material is then pressed out of the syringe at the site intended for printing. In this manner, a three-dimensional object composed of layers is produced. The advantage of this method is a simple structure, but precise dosing is possible only by means of a complex process. Moreover, if different cells are to be used to make up the structure of the three-dimensional object, further syringes must be kept in reserve and used for printing in addition to or instead of the first syringe. This increases both the structural complexity of a corresponding printer and the time required for the actual printing. Ultimately, this is reflected in high costs.

Syringe printing methods of this kind are described for example in WO 2013/113883 A1, US 2011/0313542 A1, U.S. Pat. No. 8,580,546 B2, and US 2012/0288938 A1. US 2014/0093932 A1 also describes a syringe printing method in which additional curing of the biological material already accumulated at the intended site is carried out by means of UV light.

In the laser printing method, printing is carried out by means of a laser beam. Here, a carrier film is initially coated with a liquid containing cells. After this, a laser beam pulse is directed onto the coated carrier film, causing a drop of the cell suspension to be propelled from the carrier film. The individual drops can then be stacked atop one another by means of skilled stacking—similar to the inkjet printing method. It is true that the amount of the drops of the cell suspension to be applied can be dosed with quite high accuracy. However, the drops deform during the flying phase on their way to the surface on which the object to be printed is to be produced. Because of the wobbling movement connected therewith, this in turn results in inaccuracies in positioning the drops. As the drop size as a whole is rather small, the laser printing method is very slow. Larger and more complex objects cannot be printed by this method. Moreover, no hanging structures without support structures can be produced.

The object of the present invention is to provide a printing method for a three-dimensional object composed of biological material that overcomes the drawbacks known from the prior art and in particular makes it possible to carry out high-precision object structuring and to use different materials in a simple manner in printing the objects. Furthermore, a corresponding device is to be provided with which the method can be implemented.

This object is achieved by means of a method for producing a three-dimensional, multi-cell object. In such a method, a first photopolymerizable liquid is first introduced into a reaction vessel. After this, a first light beam is focused on a first focal plane that lies within an area of the reaction vessel filled with the first liquid. By means of this light beam, a first polymerized structure is then produced in the reaction vessel. In this case, the first polymerized structure is located in a first layer.

In further process steps, a further photopolymerizable liquid is introduced into the reaction vessel, wherein the previously produced polymerized structure is at least partially covered with the further photopolymerizable liquid. The previously produced polymerized structure is preferably completely covered with the further photopolymerizable liquid. A further light beam is now focused on a further focal plane that lies in an area of the reaction vessel filled with the further liquid. The further focal plane thus differs from the first focal plane at least with respect to the already produced polymerized structure or with respect to the layer of this polymerized structure.

By means of the further light beam, a further polymerized structure is now produced in a further layer in the reaction vessel. In this case, the further polymerized structure is arranged directly on the previously produced polymerized structure and connected thereto. The bonding preferably consists of a covalent bond. In principle, however, non-covalent bonds, for example based on physical interactions, would also be conceivable.

The above-mentioned steps of introducing a further photopolymerizable liquid, focusing a further light beam, and producing a further polymerized structure in a further layer are now each repeated with one further photopolymerizable liquid until the desired three-dimensional multi-cell object is produced. By means of the different focal planes in which polymerization of the photopolymerizable liquids takes place, a layered structure of the three-dimensional, multi-cell object is therefore achieved. Here, undercuts and overhanging structures are also possible, as polymerization of the photopolymerizable liquid in a specified focal plane or layer can occur even when there is no already-polymerized material arranged thereunder, but only not yet-polymerized material. Polymerization of this photopolymerizable liquid present outside the focal plane does not take place; rather, only that photopolymerizable liquid lying inside the focal plane is polymerized. Nevertheless, the liquid present outside the focal plane serves as a temporary support for the liquid present in the focal plane, without solid support structures being required for this purpose.

The first photopolymerizable liquid and/or at least one of the further photopolymerizable liquids contain(s) biological cells. When polymerization occurs as a result of the light irradiation, the cells contained in the liquid are also embedded in a corresponding polymer. As not all photopolymerizable liquids need also contain cells, cell-free structures can be formed in the produced three-dimensional multi-cell object, for example in the form of intermediate structures.

Using this method, complex biological objects can be produced as models, for example for representing and investigating cell-cell interactions, organ biogenesis, diseases, or organ functions. Such a three-dimensional object has clear advantages over the classical two-dimensional cell culture, in particular in the case of modelling the interaction among a plurality of cell types. The reason is that the complexity of cell-cell interactions, the function of a natural barrier, and the modelling of diseases or organs cannot be sufficiently illustrated using the classical two-dimensional cell cultures.

In addition, the method described here makes it possible to produce miniaturized models in a particularly simple manner. In the past, such miniaturized models were partially produced by hand. The complexity required for such production is very high; in addition, long years of experience are required.

Finally, by means of the method described here, high reproducibility of different copies of the same three-dimensional, multi-cell object can be ensured. As a result, the method described here not only makes it possible to accelerate production compared to other methods known from the prior art, but the produced objects also always show the same quality. Such high reproducibility is particularly advantageous in biotechnology. The reason is that in the analysis and development of new pharmaceutical products, testing conducted on three-dimensional cell cultures that always remain the same considerably reduces development costs. In contrast, when such complex three-dimensional structures are constructed by hand, individual fluctuations are inevitable. However, this makes it practically impossible to achieve reproducible test results. In contrast, the method described here provides objects that are outstandingly well suited for achieving reproducible test results.

As reaction vessels, cavities (so-called wells) of common commercial microtiter plates (for example, microtiter plates with 6, 12, 24, 48, 96, 384, or 1536 wells), cell culture flasks, or Petri dishes can be used.

The three-dimensional multi-cell object produced by means of the method can be composed of a homogenous material and therefore comprise only cells of a single type. Furthermore, the polymer material surrounding the cells can be configured to be uniform. In a variant, however, the first photopolymerizable liquid and at least one of the further photopolymerizable liquids are different liquids. This makes it possible to produce heterogeneously constructed multi-cell objects comprising cells of different types. In this way, moreover, it is possible to provide identical or different cells in different surrounding polymers. This means that different liquids can differ both with respect to the polymerizable material in the liquid and with respect to the cells contained in the liquid. This variant therefore provides a method by means of which different cell types are combined to form an artificial organ. This organ can be an organ which simulates or imitates a human or animal organ. This makes it possible in a single print operation to produce different objects within the same reaction vessel or within adjacent reaction vessels.

When an artificial organ is produced by means of the present method, this organ model can be a model that represents a healthy organ. Alternatively, a disease model can also be produced in the form of an organ having a specified defect. For example, a mechanical constriction can be introduced into an object produced by the present method in order to produce a "built-in" injury such as would occur in the event of a blow with a blunt instrument or blunt trauma. In this way, it is possible to provide a standardized structure of such a disease model. It is also possible to produce a degenerative gradient within an object. For example, a relatively healthy cell structure can be produced in a first area of the object that then continuously transitions into a diseased structure via a local gradient in the object produced. In this case, intermediate, partially diseased structures would be located in the object produced between the two extreme structures. Moreover, it is also possible, by incorporating viruses or bacteria, to produce infection models for artificial organs. Such incorporation of bacteria or viruses can take place in the manner described above during the printing process by selecting a suitable further photopolymerizable liquid that contains corresponding viruses or bacteria as cells.

By selecting suitable cell types, it is also possible to produce disease models for typical diseases such as diabetes, tumors, or compromised tissue, such as would be found after a myocardial infarction or a stroke in a living organism. As cell-free photopolymerizable liquids can also be used in addition to cell-containing photopolymerizable liquids, "packaging" of the object produced in a cell-free polymer can be produced in the same print operation in which the object itself is also produced. This means that the object is generated with and in its carrier simultaneously, so that the packaging and the multi-cell object are produced in parallel.

In a variant, the photopolymerizable liquid comprises an acrylic compound by means of which the polymerization is achieved. The acrylic compound is preferably selected from the group composed of methacrylates, methyl acrylates, ethyl acrylates, hydroxyethyl acrylates, butyl acrylates, trimethylolpropane acrylates, triacrylate acrylates, and polyacrylates (PA) in general.

In a variant, the acrylic compound is coupled to a starting substance to be gelled or polymerized. In particular, this coupling gives rise to a covalent bond between the acrylic compound and the starting substance to be polymerized. Examples of this starting substance may include a carbon-based polymer such as polyethylene glycol (PEG), polyethylene (PE), polypropylene (PP), polyketone (PK), polyvinyl chloride (PVC), polystyrene (PS), polytetrafluoroethylene (PTFE), polymethyl methacrylate (PMMA), polycarbonate (PC), polyethylene terephthalate (PET), and polyurethane (PU). Synthetic polymers such as silicones, polydimethylsiloxane (PDMS), or resins such as melamine resins or melamine formaldehyde resins are also suitable as starting substances. Moreover, biopolymers such as proteins, DNA, RNA, carbohydrates and carbohydrate derivatives, collagens, fibrins, alginates, or gelatins are also suitable as starting substances. Instead of the above-mentioned polymers, the respective monomer precursors or oligomer precursors of these polymers can also be used as starting substances, as long as they can be provided in a stable manner in a solid or liquid aggregate state. The introduction of an acrylate functional group into the starting substance by means of coupling between the acrylic compound and the starting substance provides a polymerizable matrix, even if the starting substances are already polymers.

When photopolymerizable PDMS is used as a matrix or a coating substance, gas exchange is possible among the cells embedded in this matrix. As mentioned above, different coating substances or matrices can be used. For example, in addition to PDMS or another matrix showing good biocompatibility, a stable plastic can be used for the remaining matrix in order to produce an object that is stable to the exterior and in its interior contains a less stable matrix that allows cell growth. As mentioned above, it can therefore be said that in parallel to the three-dimensional multi-cell object, inherent protection thereof or its own packaging can be produced.

The starting substance with the added acrylate functional group is used in liquid form, with different viscosities being possible. This means that the method described here is not limited to liquids having a particular viscosity, but can also use low-viscosity liquids as starting substances. In this case, the flow behavior of these liquids can range from thixotropy to rheopexy.

The liquids can be solutions or colloidal dispersion mixtures such as suspensions. In this case, the liquids can have aqueous to oily properties. Among other factors, this is determined by selection of the starting substances and their particle size.

So that photopolymerization of the starting substance bearing an acrylate functional group can be achieved, a radical former (a so-called photoinitiator) is moreover used that forms radicals at a selected wavelength of the light used in the context of the method.

Examples of suitable radical formers include anthrone derivatives such as violanthrone or isoviolanthrone, fluorescein, rubrene, anthracene derivatives, tetracene derivatives, benzanthrone, benzanthronil, eosin, levulinic acid derivatives, phosphine derivatives, monoacyl- and bisacylphosphines, metallocenes, acetophenones, benzophenones, xanthones, quinones, ketone derivatives, hydroxyketones, aminoketones, benzoyl peroxides, pyridine salts, phenylglyoxylates, and/or iodonium salts.

In addition to the radical former, a vinyl macromer and an amine-based co-initiator are also preferably used in order to make the course of photopolymerization particularly suitable. Examples of suitable co-initiators include ascorbic acid and tertiary amine derivatives such as methyl diethanolamine or tetraethylamine.

In a variant, the photopolymerizable liquid comprises a thiol derivative. Suitable thiol derivates are dithiothreitol, monofunctional cysteines, bifunctional peptides, and similar compounds.

Moreover, a substance can be added to the photopolymerizable liquid that inhibits photopolymerization of the deeper, more liquid layers. This causes liquid solution outside the focal plane to remain liquid, even if it is located in the irradiation area of the focal plane above it. This is caused by absorption of the polymerizing wavelength by the substance. Interception takes place in the focal plane, so that it is not possible for the polymerizing wavelength to penetrate into deeper layers. All substances that absorb at the desired wavelength, such as dyes, are suitable.

In a further variant, the photopolymerizable liquid comprises a monofunctional monomer such as N-vinyl pyrrolidone.

In addition, it is possible in a variant for the first photopolymerizable liquid and/or one of the further photopolymerizable liquids and/or another liquid, which does not have to be photopolymerizable, to comprise a temperature-sensitive gelling agent. In particular, the use of an inverse temperature-sensitive (also referred to as reverse temperature-sensitive) gelling agent is provided. Such a gelling agent becomes increasingly solid with rising temperature. On heating of the reaction vessel, the reaction liquid solidifies and forms a gel that is initially only metastable. Should the liquid not be simultaneously photopolymerized, subsequent cooling of the object can cause the metastable gel to again become liquefied and be pumped away. In commonly used temperature-sensitive gelling agents, the temperature conditions to be used are exactly opposite. As needed, therefore, e.g. a support structure can be configured so that hanging structures can be produced. In contrast, if the metastable gel is at least partially irradiated with light of a suitable wavelength, this causes photopolymerization, so that the metastable gel is converted in these areas into a stable gel or polymer.

In other words, by means of the temperature-sensitive, in particular inverse temperature-sensitive, gelling agent and temperature control of the reaction space, it becomes possible to work more simply with hanging parts and undercuts. In this variant, however, one can also continue to work even with liquid structures as a support.

It is also possible to provide a temperature gradient so that a metastable gel does not occur in all areas of the liquid mixed with the temperature-sensitive, in particular inverse temperature-sensitive, gelling agent. By using such a gradient, even more complex structures can be produced.

The above-mentioned individual components can be contained in the photopolymerizable liquid as individual substances. Alternatively, it is also possible to implement the substances or groups preferably used for gel formation in a single polymer by means of corresponding synthesis. Instead of a mixture of individual components, such a polymer would then comprise different functional groups that combine all of the functions required or which are preferably to be used for photopolymerization. Furthermore, it is also conceivable to provide only some of the functional groups or groups preferably used for photopolymerization in one polymer, and to mix other functional groups or groups preferably used for photopolymerization into separate individual components of the photopolymerizable liquid.

As biological cells used for the structure of the three-dimensional, multi-cell object, all naturally occurring eukaryotic and prokaryotic cells are suitable. The cells used are preferably eukaryotic cells. Particularly well suited are all cells and cell types that occur in the body of a mammal, in particular a rodent and particularly preferably a human, or make up this body. In a variant, the biological cells used are omnipotent or pluripotent cells. Here, the invention relates in a variant only to the use of those cells that can be obtained without destroying human embryos. In addition to naturally occurring cells, cells of non-naturally occurring cell lines can also be used as biological cells. Such artificially generated cell lines make the tailor-made structure of the three-dimensional, multi-cell object to be produced possible.

As the present method makes it possible to combine various cell types into a three-dimensional multi-cell object, it is particularly well suited for the production of artificial organs. For example, such artificial organs can be miniaturized model objects of a naturally occurring organ, in particular a naturally occurring organ of a human or an animal such as a mammal or rodent. As different photopolymerizable liquids can be used, different gel types in which the biological cells are embedded are also possible. It is also possible to combine synthetic polymers and biopolymers, so that highly stable constructs can be produced in which the biological cells are embedded. During a single print operation, a plurality of three-dimensional objects, even having different forms, can be simultaneously produced.

Moreover, the membrane and barrier function in combination with the organ function also make it possible to simulate the model of a pregnancy using this technology.

In a variant, the artificial organs produced are in particular those organs that simulate the functions of the muscles, skeleton, skin, fatty tissue, bowel, liver, bone marrow, brain, lungs, heart, kidneys, thyroid, or spleen and can therefore be referred to as artificial muscles, artificial skeleton, etc.

On a carrier inside a reaction vessel, or also in different reaction vessels, combinations of different artificial organs, which for example are produced during the same print operation, can be provided.

In a variant, the further photopolymerizable liquid is not introduced into the reaction vessel until the photopolymerizable liquid previously present in the reaction vessel (e.g. this can be the first photopolymerizable liquid or a further photopolymerizable liquid) has been removed from the reaction vessel. For this purpose, for example, it is possible to provide a pump that pumps an already-used photopolymerizable liquid out of the reaction vessel and pumps a new further photopolymerizable liquid into the reaction vessel. For such processes, two or more different pumps can also be used instead of one individual pump.

In a variant, it is conceivable and provided to introduce a disinfectant liquid into the reaction vessel in order to allow sterile production of the three-dimensional, multi-cell object. Such a disinfectant liquid can for example be introduced into the reaction vessel when a previously used photopolymerizable liquid has been removed from the reaction vessel and a further photopolymerizable liquid has not yet been introduced into the reaction vessel. Moreover, it is also conceivable to introduce a disinfectant liquid into the reaction vessel in addition to a photopolymerizable liquid so that it is contained in the reaction vessel during the photopolymerization process.

As a disinfectant liquid, for example, an alcohol such as ethanol or propanol can be used. Here, aqueous solutions of those alcohols in which the alcohol concentration is for example in the range of 40% to 90%, in particular 50% to 80%, and very particularly 60% to 70% (v/v respectively), are in particular suitable for disinfection.

In a variant, the multi-cell three-dimensional object, during or at the end of its production process, can be irradiated with light of a short wavelength (for example in the UV region, i.e. less than 380 nm) in order in this manner to achieve sterilization. Such UV sterilizations are generally known. In the present case, however, they can be advantageously used if the biological cells contained in the three-dimensional object will not be damaged by such UV radiation.

In a variant, a carrier plate or carrier structure is arranged in the reaction vessel to which the first polymerized structure is bonded. The use of such a carrier plate is advisable in cases where the produced three-dimensional multi-cell object is not to be investigated later in the reaction vessel itself, but is to be removed from the reaction vessel. For example, screw terminals (such as DIN screw terminals) can be present in the carrier plate in order to allow subsequent supply of liquids and gases to the produced multi-cell three-dimensional object. It is also possible to introduce such screw terminals into the matrix of the three-dimensional, multi-cell object during the production process, i.e. to generate the screw terminals in the matrix during said process. The production of such screw terminals in the matrix may be carried out regardless of whether or not a carrier plate is used.

In a variant, a carrier plate is produced before the step of producing a first polymerized structure by irradiation with a light beam in a focal plane that lies within an area of the reaction vessel filled with a photopolymerizable liquid (particularly with the first or one of the further photopolymerizable liquids), by forming a polymerized carrier structure that comprises or constitutes the carrier plate. This means that in this variant, not only the actual polymerized structures, but also the carrier structure are produced by a polymerization reaction.

The carrier structure can have a form such that a distance is produced between the carrier plate and a bottom of the reaction vessel. This then causes the focal planes of the actual polymerization reactions to be at a greater distance from the bottom of the reaction vessel. In particular, the first formed polymerized structure is then at a greater distance from the bottom of the reaction vessel. This makes it possible to particularly easily suction off polymerizable liquids that are no longer needed from the reaction vessel.

So that the liquids can readily penetrate through the carrier plate or the carrier structure, the carrier structure can be provided with liquid-permeable openings, particularly in the area of the carrier plate.

In a variant, an optical system is arranged between a light source for producing the first and/or the further light beam and the reaction vessel, said optical system serving to focus the light beam on the respective focal plane in the reaction vessel. Here, it is provided in a variant that refocusing of this optical system can be carried out in order to change the focal plane inside the reaction vessel. For example, such refocusing can be achieved by changing the distance of the optical system from the light source. Here, a computer-controlled stepper motor can be provided in order to provide a corresponding movement of the optical system. The optical system can for example comprise a system of optical lenses—or in the case of a particularly simple construction, an individual focusing lens.

When refocusing of an optical system is carried out in order to change or shift the focal plane inside the reaction vessel, there are ordinarily no particular requirements for the configuration of the reaction vessel.

In a variant, it is also possible to carry out a relative movement between the reaction vessel or a carrier plate arranged in the reaction vessel on the one hand and a light source for producing the first and/or the further light beam on the other hand. The reason is that by means of such relative movement, which can be carried out for example by a movement of the reaction vessel, a movement of the carrier plate arranged in the reaction vessel, or a movement of the light source, it is also possible to change the focal plane inside the reaction vessel. In this variant, therefore, no refocusing of an optionally used optical system is required. In this way, the risk of optical misalignments can be reduced.

In a further variant method, the first and/or the further light beam is directed onto a defined and predefinable area in the respective focal plane within the first photopolymerizable liquid and/or the further photopolymerizable liquid. This means that a specific light pattern can be predetermined that strikes the photopolymerizable liquid and induces polymerization of the liquid at these sites to form a polymer or a gel (the matrix). For example, such a light pattern can be produced by the use of masks or screens, but also by the use of a pulsed light beam or the digital modulation of a light signal. Polymerization occurs at the areas of the photopolymerizable liquid struck by the light beam. At the other areas not struck by the light beam, however, the photopolymerizable liquid remains in its unpolymerized state. The light beam thus defines the areas in which printing of the polymerized structure takes place. Such light-supported printing makes it possible to achieve much higher resolutions than are possible using the methods known from the prior art. Here, the resolution depends on the wavelength of the light used. Even in the case of regularly used long wavelengths, it is better than the resolution that can be achieved with the conventional methods known from the prior art. The more precisely the light source can be focused, the greater the resulting resolution. For example, extremely high resolutions can be achieved using a laser.

As needed, the light beam can be directed onto the respective focal plane using mirrors.

The respectively selected exposure pattern can be provided for example by a computer program. Here, it is conceivable that a user produces the three-dimensional object to be produced by means of a CAD program. The digital object produced in this manner is then divided into individual exposure planes by a suitable computer program. Furthermore, a specified photopolymerizable liquid or a specified cell type is assigned to each plane or different areas of such a plane. Based on these data, control data are prepared for a printer by means of which the described method is carried out. These control data specify when and what photopolymerizable liquid must be introduced into the reaction vessel. Furthermore, these control data specify when and what image of an exposure plane is to be projected onto the respective focal plane in the reaction vessel. In this manner, the digital object previously produced on the computer can be converted into a real three-dimensional multi-cell object.

In a variant, more than one polymerized structure is produced in the same layer (i.e. in the same focal plane). To this end, polymerization of a first photopolymerizable liquid and for example embedding of a first cell type in the polymer formed from the first liquid first take place. After this, the first photopolymerizable liquid is removed from the reaction vessel and a second photopolymerizable liquid is fed into the reaction vessel. Only the areas inside the focal plane in the reaction vessel that have not previously been exposed and therefore do not yet show any polymerized structure are now exposed. This makes it possible to produce different cell types or different matrices in one and the same layer. A plurality of polymerized structures is therefore formed in one and the same layer, which results in a heterogeneous layer. After this, the second photopolymerizable liquid is removed from the reaction vessel, and a further photopolymerizable liquid is fed into the reaction vessel. The filling level of this further photopolymerizable liquid can only be brought to a level such that the previously formed layer is completely covered. The focal plane can then be shifted, and a further layer of the three-dimensional, multi-cell object to be produced can be constructed by means of a corresponding polymerized structure. In this case, it is generally possible for individual layers of the produced three-dimensional object to be homogeneous (comprising a polymerized structure of a single type) and for other layers to be heterogeneous (comprising polymerized structures of a different type), wherein the number of individual structures per layer is not limited. In practice, in addition to a single polymerized structure per layer, heterogeneously composed layers with 2, 3, 4, 5, 6, 7, 8, 9, or 10 polymerized structures have been found to be advantageous.

In a variant, at least the first structure in the first layer, but in particular each structure of the first layer, is irradiated from two different directions with the first light beam. Here, these two different directions are preferably opposite to each other. Such irradiation from two different directions provides a particularly solid anchoring of the first layer on the inner surface of the reaction vessel or on a carrier plate arranged in the reaction vessel. This allows subsequent strong adherence of the entire three-dimensional, multi-cell object produced to the reaction vessel or to a carrier plate in the reaction vessel to be achieved, which facilitates subsequent investigations of the object. Typically, the irradiation is carried out from above in a reaction vessel open at the top. In this variant, the first layer is then preferably also irradiated from below through the bottom of the reaction vessel. To this end, the reaction vessel must be made of a material that is permeable to the light beam of the selected wavelength. The subsequent layers arranged above the first layer are then in turn preferably irradiated from only one direction (i.e. preferably from above), so that the already formed polymerized structures do not lie between the focal plane of the light beam and a light source used to emit the light beam and therefore are not again irradiated by the light beam before its focal plane.

In a variant, the first light beam and/or the further light beam has a wavelength in the range of 200 nm to 1000 nm (i.e. a wavelength between the UV region and the infrared region). The substances preferably used as radical formers can be excited particularly effectively by such wavelengths, causing radicals to be formed in order to allow polymerization of starting substances bearing acrylate functional groups.

Further suitable wavelengths of the light beam used are in the range of 250 to 950 nm, in particular 300 to 850 nm, in particular 350 to 800 nm, in particular 400 to 750 nm, in particular 450 to 700 nm, in particular 500 to 650 nm, and particularly preferably 500 to 600 nm.

As UV light can damage biological cells, in a variant, only light having a wavelength in the visible region, i.e. approx. 380 nm to approx. 780 nm, is used. UV filters can also be provided in this case that filter out UV components from a light beam in order to safely filter possibly harmful UV irradiation out of the light beam used.

The light beams used for polymerization can have the same wavelength, but may alternatively comprise wavelengths different from the above-mentioned wavelength range, in order to allow suitable polymerization of the various photopolymerizable liquids. Here, the individual light beams can be produced by different light sources or by one and the same light source. It is also possible to successively use different wavelengths within one layer (and thus within one focal plane) in order to polymerize different photopolymerizable liquids in the same layer if a heterogeneous layer is to be formed from different polymerized structures.

In a variant, the method is carried out such that during the production of the three-dimensional, multi-cell object, at least one functional element is introduced into the three-dimensional multi-cell object. The functional element is in this case selected from the group composed of membranes, channels, pores, sensors, electrically conductive carriers, and chemotactic preparations. For example, channels and pores can be integrated into the object by leaving certain areas of the polymerized structure formed in a plurality of layers atop one another exposed.

Membranes can be formed by introducing lipid molecules into the photopolymerizable liquid.

In addition, by means of photopolymerization, salt bridges can also be introduced inside the object. This can be carried out in a particularly simple manner if the photopolymerizable liquid contains salts, i.e. is saline. In this manner, subsequent electrical discharge and enervation of the printed object can be carried out.

By means of sensors installed in the object during the production process, no subsequent further manipulation of the three-dimensional object produced is necessary, as it can be directly read by means of the already installed sensors. This substantially facilitates subsequent analyses of the three-dimensional object.

By introducing electrically conductive carriers such as electrodes, it is particularly simple in subsequent investigation of the three-dimensional, multi-cell object formed to analyze the electrical potential or the electrical properties of the object.

By introducing chemotactic preparations, which in a variant can be introduced in different layers in different concentrations in order to thus form a gradient, it becomes possible to carry out targeted growth of cells inside the multi-cell three-dimensional object after production thereof. If the chemotactic preparation is an attractant, it exerts positive chemotaxis, so that the cells in the three-dimensional object are oriented toward areas of higher concentration of the attractant. If the chemotactic preparation is a repellent, it exerts negative chemotaxis, so that the cells in the three-dimensional object are oriented toward areas of lower concentration of the repellent or areas in which the repellent is not present at all. This makes it possible to achieve targeted growth of cells inside the multi-cell object.

At least one filling level sensor is preferably used for constant precise determination of the liquid level in the reaction vessel. Based on this filling level data, the focal plane can then be determined in which the next polymerization step should be carried out. The data provided by such a filling level sensor can also be used to automatically adjust the focal plane. The data provided by a filling level sensor can also be used to control a pump that provides the inflow of the photopolymerizable liquids into the reaction vessel. This makes it possible to always introduce into the reaction vessel the exact amount of the photopolymerizable liquids required for forming the layer desired at a particular time. This keeps the amounts of waste to a minimum. Furthermore, this makes it possible to carry out the entire method in an economical manner.

As can be seen from the above presentation of the method described herein, this method can be carried out in a fully automated manner, so that no action by a user is required. This makes the method even easier to use.

The time during which the light beam is directed onto the respective focal plane can be adjusted to the respective requirements of the photopolymerizable liquid used. This means that each material is allowed the curing time that is required and advantageous for the desired polymerization.

If a carrier is arranged inside the reaction vessel, negative pressure can be generated between a surrounding fluid bed and the already polymerized structures on the carrier when this carrier is lifted relative to the reaction vessel. However, a potentially prevailing negative pressure can be relieved by suctioning off the residue of the photopolymerizable liquid still present in the reaction vessel from the previous polymerization step and introducing a new photopolymerizable liquid. For this reason, the carrier can be moved relative to the reaction vessel without the risk of tearing of the already polymerized structures of the three-dimensional object away from the carrier.

If the three-dimensional object is produced on a carrier plate, this carrier plate can be lifted completely out of the remaining liquid in the reaction vessel after the end of the production process. After this, the produced object can be removed from the carrier plate by the user. In order to prevent the object from being destroyed on removal from the carrier plate, the carrier plate can be configured such that a sterile air stream can be guided between the surface of the carrier plate and the underside of the produced three-dimensional object. This then allows the object to be evenly pressed away from the carrier plate, thus ensuring gentle removal of the three-dimensional object from the carrier plate.

The object of the invention is also achieved by means of a device for producing a three-dimensional, multi-cell object from photopolymerizable liquids having the following features.

Such a device comprises a reaction vessel and a light source, which is arranged such that during operation of the device, it can irradiate light into the reaction vessel, wherein this light is focused on a focal plane inside the reaction vessel. The device further comprises a reservoir for different photopolymerizable liquids. Furthermore, a pump is provided that can be brought into fluid communication with both the reservoir and the reaction vessel. For this purpose, suitable valves can be provided between the pump and the reservoir or between the pump and the reaction vessel. This makes it possible by means of the pump to introduce the different photopolymerizable liquids into the reaction vessel and discharge them from the reaction vessel. Finally, a control unit for controlling the light source and the pump is also provided.

The basic functions of the individual elements of this device have already been presented in connection with the explanations of the above-described method.

If the reaction vessel is a well of a microtiter plate, in a variant, a plurality of different lines can be provided that can be controlled via various valves so that it is possible to simultaneously fill or empty the different reaction vessels. Furthermore, a single filling or suctioning device can also be provided that can be moved to the various wells of a microtiter plate.

Supply and/or removal of photopolymerizable liquids from the reaction vessel preferably takes place in an area of the reaction vessel close to the bottom. This is because in this manner, it can be ensured on the one hand that even residual amounts of a photopolymerizable liquid to be removed can be removed from the reaction vessel. In addition, in this manner, gentle supply of a new photopolymerizable liquid into the reaction vessel can be ensured so that already polymerized structures are not damaged by the newly supplied liquid.

In a variant, the light source is provided and configured to emit light of different wavelengths. The wavelength of the light to be emitted in this case can be predetermined by a user or by a control program. This allows different polymerization wavelengths to be implemented without having to use different light sources for this purpose.

In a variant, at least one mirror is provided in order to direct the first and/or the further light beam onto the photopolymerizable liquids. In this manner, even more different arrangements of the light source and reaction vessel can be implemented.

The above-described device is particularly well suited for producing an artificial organ or a pregnancy model, as was already described above in the overview of the methods described there. Here, the artificial organ can be a healthy organ model or a disease model.

Preferred or alternative embodiments of the method described herein are applicable analogously to the device or use described, and vice versa. Here, any desired combinations of the individual variants are conceivable and provided.

Figure 2:
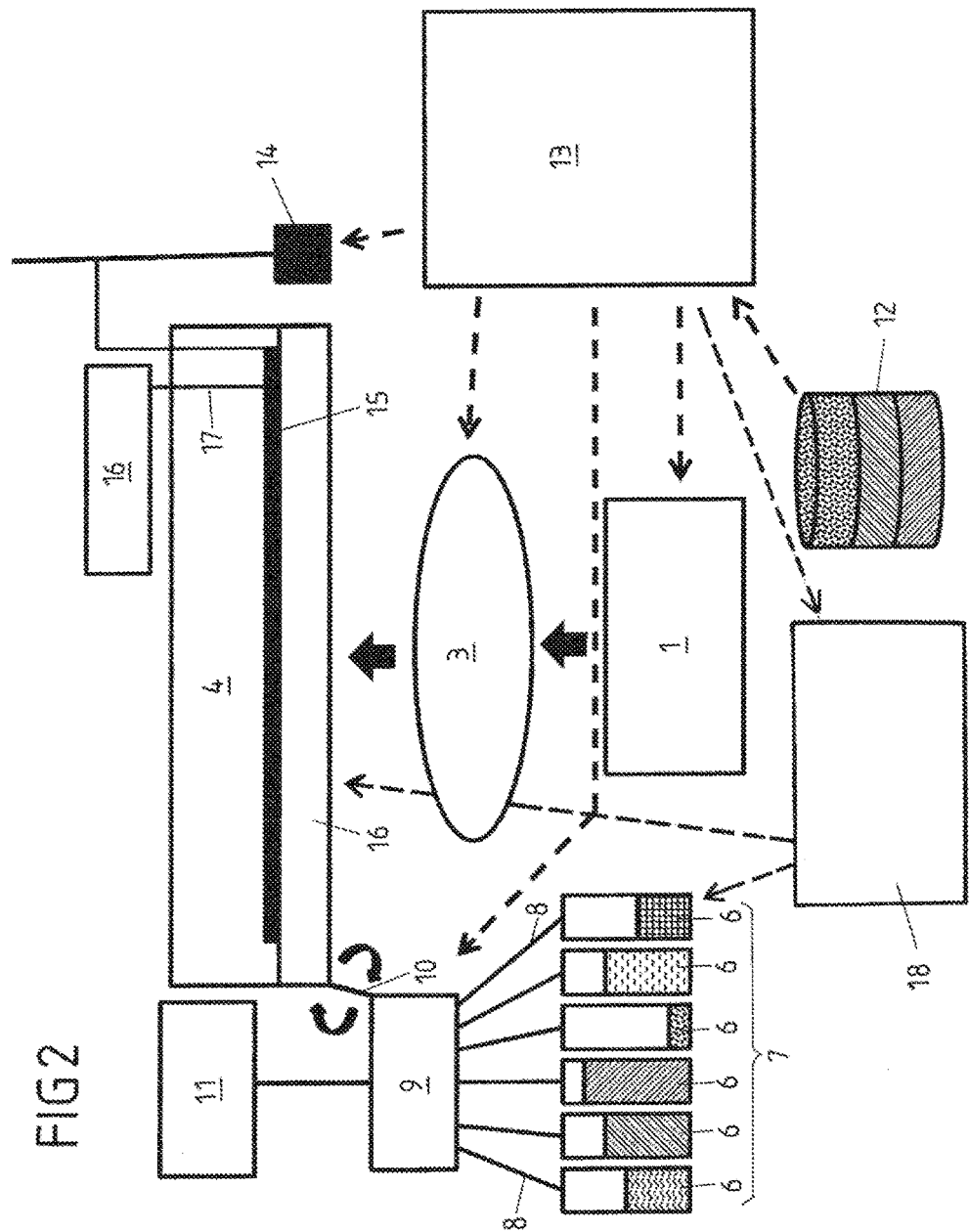
Figure 3:
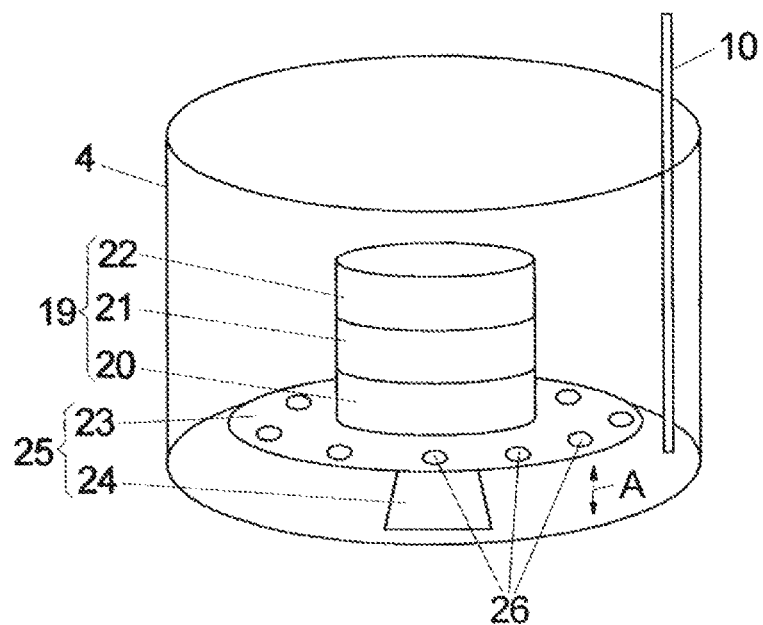

Further details of the present invention will now be explained in further detail based on illustrative embodiments and corresponding figures. The figures show the following:

FIG. 1 a first illustrative embodiment of a device for producing a three-dimensional, multi-cell object from photopolymerizable liquids, FIG. 2 a second illustrative embodiment of a device for producing a three-dimensional, multi-cell object from photopolymerizable liquids, and FIG. 3 an illustrative embodiment of a variant method in which a carrier structure is printed.

FIG. 1 shows the schematic structure of a 3D printer as a device for producing a three-dimensional, multi-cell object from photopolymerizable liquids. The 3D printer comprises a first light source 1 and a second light source 2. Light emitted by the first light source 1 is directed via a first lens 3 onto a plurality of reaction vessels 4, only three of which are shown in the illustration of FIG. 1. In the same manner, light emitted by the second light source 2 is directed via a second lens 5 onto the reaction vessels 4. Instead of two different light sources 1, 2, a single light source could also be used, wherein the beam path would then be configured such that the light emitted by this single light source would be optionally directed from the upper side of the reaction vessels 4 and/or from the underside of the reaction vessels 4 onto the reaction vessels 4.

The first light source 1 and the second light source 2 can emit light of different wavelengths, wherein the wavelength can be automatically regulated.

A plurality of different chambers 6, which respectively contain different starting liquids as photopolymerizable liquids, combine to form a reservoir 7 that is connected to a pump 9 by a number of lines 8 corresponding to the number of chambers 6. By means of the pump 9, the photopolymerizable liquids contained in the chambers 6 of the reservoir 7 can be transported via the lines 8 to the reaction vessels 4. For this purpose, the reaction vessels 4 are connected to the pump 9 via a corresponding line system 10. The pump 9 is further connected to a waste receptacle 11 into which the no-longer-needed liquid residues can be fed. Specifically, the pump 9 also serves to suction out no-longer-needed photopolymerizable liquid from the reaction vessels 4 via the line system 10 and then to feed it to the waste receptacle 11.

In operation of the 3D printer shown in FIG. 1, data on a digital object 12 produced by means of a CAD program are first transmitted to a central control unit 13. In this central control unit 13, decomposition of the digital object 12 into individual planes can then take place, provided that this has not already taken place by means of the transmitted data. In this case, the central control unit 13 serves to activate the first light source 1, the second light source 2, and the pump 9. In addition, the second lens 5 can also be moved by the central control unit 13 if this is desired by a user. The photopolymerizable liquid required for the first layer of the three-dimensional object to be produced, which already contains the cells to be introduced into the first layer, is now suctioned from the corresponding chamber 6 of the reservoir 7 by means of the pump 9 and conveyed to the individual reaction vessels 4 via the corresponding line 8 and the line system 10. After this, both light from the first light source 1 and light from the second light source 2 are focused on the reaction vessels 4, so that polymerization of the photopolymerizable liquid located in the reaction vessels 4 takes place and the polymerized structure thus formed adheres solidly to the inner side of the reaction vessel 4. After this, the remaining unpolymerized liquid is suctioned by the pump 9 via the line system out of the reaction vessels 4 and fed to the waste receptacle 11.

In accordance with the data predetermined by the central control unit 13, a further photopolymerizable liquid is now suctioned by the pump 9 from the corresponding chamber 6 of the reservoir 7 and again supplied to the reaction vessels 4 via the corresponding line 8 and the line system 10. The central control unit 13 now causes the focal plane of the light incident on the reaction vessels to be changed. For this purpose, the central control unit 13 activates a motor 14 that causes the reaction vessel 4 to be lowered by a height that corresponds to the thickness of the polymerized structure of the first layer produced in the first step. Light from the first light source 1 is now irradiated from above onto the reaction vessels 4 in order to produce a second layer of a polymerized structure, which is formed immediately above the first layer and is covalently bonded to the first layer by means of a chemical reaction.

The second light source 2 is no longer required for this step, because two-sided irradiation is to be carried out only for the bottom layer, as this layer is to adhere particularly strongly to the inner side of the reaction vessel 4. After this, not yet polymerized liquid is again pumped out of the reaction vessels 4, and a further polymerizable liquid is introduced into the reaction vessels 4 according to the values predetermined by the central control unit 13. The reaction vessels 4 are then again lowered so that the focal plane changes and a further layer can be formed. These steps are repeated until the desired three-dimensional object is produced.

As discussed above, a plurality of polymerization steps can also be carried out successively in the same layer here in order to produce a heterogeneous layer of different polymerized structures. Furthermore, different successive layers can be produced from the same photopolymerizable liquid. In such a case, it is not necessary to suction the liquid not yet polymerized in a first polymerization process out of the reaction vessels 4. Rather, the reaction vessels 4 can simply be lowered in order to change the focal plane, so that a further layer of a polymerized structure is then produced on the previously formed layer using the remainder of the photopolymerizable liquid still present in the reaction vessels.

In addition, the central control unit 13 also serves to activate a temperature regulating unit 18, which can cool and/or heat the reaction vessels 4 or a space surrounding the reaction vessels 4 and/or the reservoir 7 and/or the chambers 6 of the reservoir 7 in order to provide defined reaction conditions. The temperature regulating unit 18 makes it possible in a particularly simple manner to use temperature-dependent gelling agents and to form temperature-dependent, metastable gels.

FIG. 2 shows a further 3D printer as a further illustrative embodiment of a device for producing a three-dimensional, multi-cell object from photopolymerizable liquids. Here, the same elements are designated with the same reference symbols as in FIG. 1, with reference being made in this connection to the above explanations with respect to FIG. 1.

The 3D printer shown in FIG. 2 differs from the 3D printer shown in FIG. 1 particularly in the configuration of the reaction vessel 4. Specifically, in the 3D printer shown in FIG. 2, a carrier plate 15 is arranged inside the reaction vessel 4 that serves as a substrate for the three-dimensional object to be produced. Here, irradiation with light from the first light source 1 takes place from an underside of the reaction vessel 4. This means that the three-dimensional object to be produced is produced with the upper side facing downward inside the reaction vessel 4. The bottom layer of the object to be produced is first polymerized on the carrier plate 15. After this, the carrier plate 15 is lifted by means of the motor 14 so that the next layer is then produced on the layer already adhering to the carrier plate 15. This means that in this case, the focal plane of the light radiating from the light source 1 into the reaction vessel 4 is shifted by lifting of the carrier plate 15. Here, the carrier plate 15 is lifted only so far that a layer of a polymerized structure already formed thereon just touches the surface of a polymerizable liquid 16 located in the reaction vessel 4. When the light from the light source 1 is then radiated into the reaction vessel 4, the further layer of a polymerized structure formed thereby is directly deposited on the already previously produced layer, so covalent bonding of the two layers to each other can take place, thus imparting high stability to the final produced object.

As only a single reaction vessel 4 is provided for the 3D printer of FIG. 2, the line system 10 that connects the pump 9 to the reaction vessel 4 is also only a single line.

In order for the object produced on the carrier plate 15 to be easily removable from the carrier plate 15, a sterile air pressure source 16 is also provided that can be brought into fluid communication with the carrier plate 15 via an air pressure line 17. When production of the three-dimensional object is completed, air can be forced via the sterile air pressure source 16 between an underside of the carrier plate 15 and the first layer of the produced object, so that the object can be easily removed from the carrier plate 15.

In both the illustrative embodiment of FIG. 1 and the illustrative embodiment of FIG. 2, in addition to the functions mentioned above, the central control unit 13 is also used to control the image or pattern produced by the light source, the duration of exposure, the height of the reaction vessel 4 or the carrier 15 inside the reaction vessel 4, the focal plane, the filling level of the photopolymerizable liquid 16 inside the reaction vessel 4, the selection of the photopolymerizable liquid, and/or the valves provided in the lines 8 and the line system 10. In this manner, the 3D printers can operate fully automatically and produce a three-dimensional object without interaction with a user based on correspondingly supplied data.

As in the illustrative embodiment of FIG. 1, a temperature regulating unit 18 is provided. Reference is made to the above explanations in this connection.

By means of the further illustrative embodiment explained below, a possible temperature sensitivity of the photopolymerizable liquid used is presented.

By the addition of a temperature-sensitive substance, in particular an inverse temperature-sensitive substance, the production of hanging objects and hollow chambers can be further improved. For example, a substance such as a poloxamer can be mixed in here in a concentration such that the photopolymerizable liquid or a non-photopolymerizable liquid gels in a desired temperature range even without light irradiation.

For example, the course of the method can be as follows: If gelling is to be achieved at a temperature of approx. 20° C., a poloxamer is mixed into the photopolymerizable liquid in a concentration such that the liquid gels in this area. Mixtures of a plurality of poloxamers are also possible. If possible, the liquid can first be cooled to a temperature below the gel point. If a hanging structure inside the object is desired, the liquid containing the temperature-sensitive gelling agent can be heated to a temperature above the gelling temperature. The liquid then gels. Parallel to this, the liquid can also be photopolymerized. If an area of the temperature-sensitive liquid is not photopolymerized, this liquid will be solid at the elevated temperature, but can be again liquefied at any time by decreasing the temperature below the gelling temperature. The temperature-sensitive, gelled component can therefore function as a support structure until the end of the printing process. After printing is completed, the temperature can again be decreased below the above-mentioned illustrative gelling temperature of 20° C. As a result, the non-polymerized, temperature-sensitive portion of the liquid liquefies again and can be pumped away. If the gel is liquefied, the support structure is removed, and the formerly supported portion of the printed object, which is now photopolymerized, hangs free.

FIG. 3 shows an object 19 printed in a reaction vessel 4. The printed object 19 is composed of a plurality of superposed polymerized structures 20, 21, 22, which are shown only schematically in the illustration of FIG. 3. The bottom polymerized structure is formed on a platform 23 that serves as a carrier plate. The platform 23 is connected via a centrally arranged stand 24 to the bottom of the reaction vessel 4. The stand 24 provides a distance A between the platform 23 and the bottom of the reaction vessel 4.

Together, the platform 23 and the stand 24 form a carrier 25, which can also be referred to as a carrier structure. Holes 26 are formed in the platform 23 through which liquids can flow to the bottom of the reaction vessel 4. The liquids can then be suctioned off in a particularly simple manner through a line system 10 (also cf. FIGS. 1 and 2 in this respect). In this way, moreover, fresh liquids can be simply introduced via the line system 10 into the reaction vessel and be well distributed, as the bottom polymerized structure 20 then does not hinder liquid distribution.

The invention claimed is:
1. A method for producing a three-dimensional, multi-cell object, comprising the following steps:
 a) introducing a first photopolymerizable liquid into a reaction vessel,
 b) focusing a first light beam on first selected regions of a first focal plane that lies within an area of the reaction vessel filled with the first liquid,
 c) producing a first polymerized structure in a first layer in the reaction vessel by way of the first light beam in the selected regions,
 d) discharging uncured first photopolymerizable liquid from the reaction vessel,
 e) introducing a further photopolymerizable liquid into the reaction vessel, so the area outside of the previously produced polymerized structure first focal plane is filled with the further photopolymerizable liquid, f) focusing a further light beam on the focal plane that lies within an area of the reaction vessel filled with the further liquid, g) producing a further polymerized structure in a further layer in the reaction vessel by way of the further light beam, wherein the further polymerized structure is arranged directly adjacent the previously produced polymerized structure and is connected thereto, and h) raising the polymerized structure the thickness of one layer and repeating steps d) through g) with the same or different photopolymerizable liquids until the three-dimensional multi-cell object is produced, wherein the first photopolymerizable liquid and/or at least one of the further photopolymerizable liquids contain biological cells;

characterized in that more than one polymerized structure is produced in the same layer.

2. The method as claimed in claim 1, wherein the first photopolymerizable liquid and at least one of the further photopolymerizable liquids are different liquids.

3. The method as claimed in claim 1, wherein the further photopolymerizable liquid is not introduced into the reaction vessel until the photopolymerizable liquid previously present in the reaction vessel has been removed from the reaction vessel.

4. The method as claimed in claim 1, wherein a carrier plate is arranged in the reaction vessel to which the first polymerized structure is bonded.

5. The method as claimed in claim 1, wherein refocusing in an optical system, which is arranged between a light source for producing the first and/or the further light beam and the reaction vessel, is carried out in order to change the focal plane inside the reaction vessel.

6. The method as claimed in claim 1, wherein a relative movement between the reaction vessel or a carrier plate arranged in the reaction vessel on the one hand and a light source for producing the first and/or the further light beam on the other hand is carried out in order to change the focal plane.

7. The method as claimed in claim 1, wherein the first and/or the further light beam is directed onto a defined and predefinable area in the respective focal plane within the first photopolymerizable liquid and/or the further photopolymerizable liquid.

8. The method as claimed in claim 1, wherein at least the first polymerized structure in the first layer is irradiated from two directions with the first light beam.

9. The method as claimed in claim 1, wherein the first light beam and/or the further light beam has a wavelength in the range of 200 to 1000 nm.

10. The method as claimed in claim 1, wherein the first light beam and/or the further light beam has a wavelength in the range of 380 to 780 nm.

11. The method as claimed in claim 1, wherein during the production of the three-dimensional, multi-cell object, at least one element is integrated into the three-dimensional multi-cell object that is selected from the group composed of membranes, channels, pores, sensors, electrically conductive carriers, and chemotactic preparations.

* * * * *